United States Patent [19]

Goldberg

[11] Patent Number: 5,425,707
[45] Date of Patent: Jun. 20, 1995

[54] METHOD FOR NON-SURGICAL TREATMENT OF CARPAL TUNNEL SYNDROME

[76] Inventor: Larry Goldberg, 2441 Olive St., Philadelphia, Pa. 19130

[21] Appl. No.: 83,748

[22] Filed: Jun. 28, 1993

[51] Int. Cl.⁶ .......................................... A61M 31/00
[52] U.S. Cl. ..................................... 604/51; 128/898; 128/878; 128/DIG. 26
[58] Field of Search ............... 128/846, 869, 877–879, 128/898, DIG. 26; 604/49, 51

[56] References Cited

U.S. PATENT DOCUMENTS

| | | |
|---|---|---|
| 2,226,230 | 12/1941 | Mazzeo . |
| 2,262,231 | 12/1941 | Mazzeo . |
| 3,480,013 | 10/1969 | Garber . |
| 3,901,227 | 8/1975 | Klatskin . |
| 4,369,774 | 1/1983 | Robbins . |
| 4,928,712 | 5/1990 | Mele . |
| 4,962,770 | 10/1990 | Agee et al. ........................... 128/898 |
| 5,025,801 | 6/1991 | Callaway . |
| 5,089,000 | 2/1992 | Agee et al. . |
| 5,179,963 | 1/1993 | Berger ................................. 128/898 |
| 5,256,136 | 10/1993 | Sucher ................................ 128/879 |

Primary Examiner—C. Fred Rosenbaum
Assistant Examiner—Chalin Smith
Attorney, Agent, or Firm—Robert F. Zielinski

[57] ABSTRACT

An apparatus and method of use for treating carpal tunnel syndrome designed to permit delivery of a sustained release, depot form of a corticosteroid agent at an adequate therapeutic dosage, directly into the center of the carpal tunnel. The apparatus consists of an armboard adapted for receiving and securing a human forearm and hand. In a preferred embodiment, the armboard also includes at least one forearm bracket and at least one wrist bracket having an integrally formed centering pointer and needle guide for delivery of medication into the carpal tunnel. In one embodiment of the method of use, an anesthetic agent and a corticosteroid are delivered by a needle installation directly into the anatomic center of the carpal tunnel in order to produce the desired pharmacological effects.

8 Claims, 5 Drawing Sheets

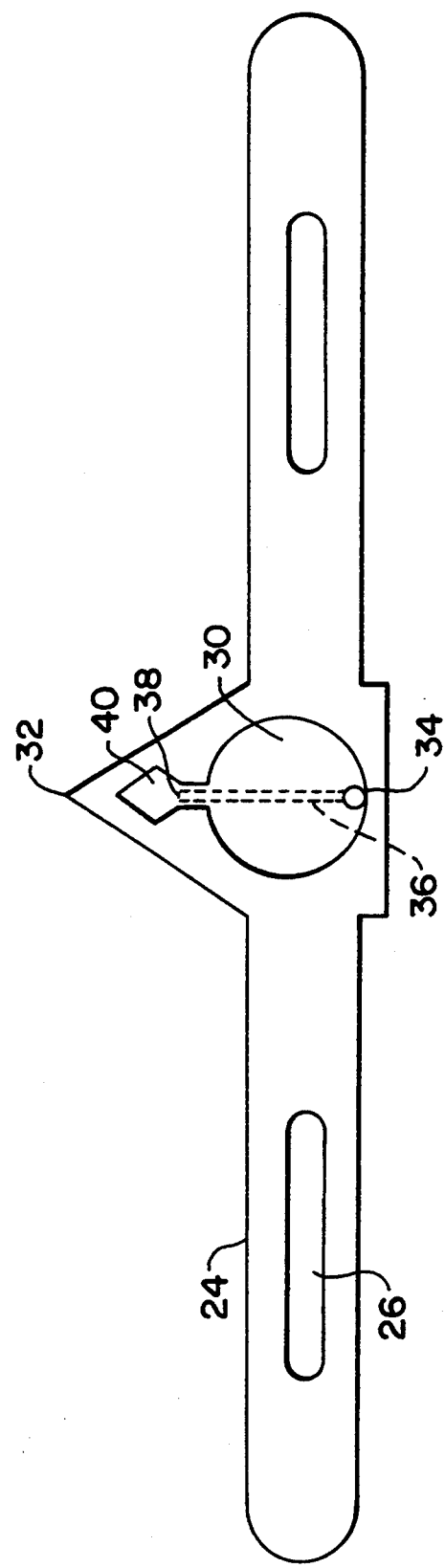

METHOD FOR NON-SURGICAL TREATMENT OF CARPAL TUNNEL SYNDROME

This invention pertains generally to a method of treatment for carpal tunnel syndrome and, more specifically, to a non-surgical method and apparatus for such treatment the use of which permits therapeutic agents to be delivered directly into the carpal tunnel.

BACKGROUND OF THE INVENTION

Carpal tunnel syndrome is among the most frequently encountered neuro-musculoskeletal disorders. Initially described by Sir James Paget in 1853, the syndrome of median nerve entrapment has been recognized traditionally as primarily a disease of middle life. Recently however, its incidence and prevalence have been increasing among both younger persons and those beyond middle life.

The increase in occurrence of carpal tunnel syndrome has been coincident with a number of factors including lengthening life expectancy. However, a particularly significant factor appears to be the ubiquity of the computer keyboard in both the home and the office. Indeed, because of the wide spread use of the computer in the home and in clerical and office employment, the incidence of carpal tunnel syndrome has increased dramatically. Moreover, it is estimated that afflicted females out number males at a ratio of from 3:1 to 5:1.

The carpal tunnel is a semi-nondistensible, open-ended and approximately cylindrical anatomical compartment bounded by the carpal bones and the flexor retinaculum, a.k.a. the flexor carpal ligament. The carpal tunnel is situated beneath the soft tissues at and just proximal to the wrist, with its long axis parallel with the axial plane of the arm. The carpal tunnel is traversed by the flexor tendons of the hand, the vascular supply of the median nerve and the median nerve itself. The median nerve supplies sensory and motor functional innervations to a substantial and rather distinct portion of the human hand. In the transverse plain, at the level of the distal forearm, the median nerve lies immediately beneath the flexor retinaculum; the flexor tendons to the hand lie deep to the median nerve.

The median nerve is the softest structure within the carpal tunnel, and when intraluminal pressure becomes augmented or increased, the vectors of force are exerted upon and against the median nerve and its blood supply. Patients with carpal tunnel syndrome suffer from elevated intraluminal pressure, such as that resulting from inflammation due to a myriad of potential underlying pathophysiological etiologies, or all too often, without any apparently identifiable reason. Specifically, where intraluminal pressure within the carpal tunnel increases, the consequential impingement of the median nerve and its blood supply leads to circulatory compromise in the median nerve. This compromise in blood flow in turn, slows the rate of median neural conduction which is manifested by an objective functional impairment of the hand. This impairment may be acutely exacerbated by certain mechanical stresses.

The most frequent complaints of carpal tunnel syndrome are hand pain and a numbness characterized by the classic "text book description" of carpal tunnel syndrome which includes: burning, nocturnal hand pain, which generally is sufficient to awaken the patient from sleep, and which may be temporarily relieved by shaking or suspending the hand and forearm in a dependent position. This pain may also radiate proximally to the forearm or elbow, and, at times, even as far as the shoulder. Numbness occurs along the distribution of the median nerve, which includes the anterior surfaces of the thumb, index finger, middle finger, and the radial half of the ring finger, as well as the distal palm. Loss of tactile sensation or thenar muscle atrophy often results in patient complaints of clumsiness or incoordination of the affected hand(s). Muscular wasting is a relatively late phenomenon in the development of the carpal tunnel syndrome disease process.

Traditionally, treatments employed for carpal tunnel syndrome have been classified as either curative or palliative. Of the curative treatments, surgical release and decompression is considered the only viable and therefore accepted method. One example of a recent development in the surgical treatment of carpal tunnel syndrome is disclosed in U.S. Pat. No. 5,089,000 to Agee et. al. However, even an intervention so seemingly definitive as surgery does not enjoy unequivocal success as propitious therapy for carpal tunnel syndrome. Although conventional operative release and decompression of the carpal tunnel has been deemed the only curative modality available, it appears that surgical success, as that term is used in authoritative text in professional journals describe operative results or outcomes which fall short of permanent abatement of all clinical manifestations of carpal tunnel syndrome. It is estimated that as many as approximately 30% of the cases treated via surgery have failed that modality. In other words, surgical success and operative cure are not synonymous terms in the applicable literature.

Even in those published reports which fail to specifically delineate qualifications for successful surgical treatment, a low threshold for categorization of a surgical result as successful may be inferred from the usual very narrow definition of a surgical failure. Most often a case is considered to have failed surgically where no identifiable improvement occurs immediately after surgery, or where symptoms recur during the proximate post-operative convalescent period.

Moreover, because the surgical methods used to treat carpal tunnel syndrome necessarily give rise to some tissue damage and scarring in or about the carpal tunnel, the resultant inflammatory response increases intraluminal pressure post-surgically. This increase in some individuals is permanent, thereby exacerbating this condition in a number of patients.

In sum, surgical treatment for carpal tunnel syndrome, although potentially curative in some cases, is probably more often in reality, a palliative technique which is ineffective in a large fraction (up to 30%, or more over time) of patients. Clearly, operative management of carpal tunnel syndrome has a number of inevitable and potential drawbacks all of which are self-evident.

Carpal tunnel syndrome has recently become the second leading cause of time lost from work due to disability. Employment-related carpal tunnel syndrome presents a number of heretofore unresolved problems relating to a number of factors. Central among these factors is that no known therapeutic modality adequately treats the problem. Specifically, for example, following surgery for employment-associated carpal tunnel syndrome, the patient-employee suffers early reoccurrence of his/her symptoms, even where the work load and duration of work stress have been dramatically reduced. The relevant medical literature has not offered any substantial explanation or recommendation therefore directly. However, two relatively contemporaneous reports, do explain the situation. For example, computerized axial tomography (CAT) scans of the carpal tunnel were obtained before and after surgery for work-related carpal tunnel syndrome. The CAT scans demonstrated that, following division of the flexor retinaculum, the contents of the carpal tunnel subluxed distally and palmarly. Considering this displacement in light of the poor results following carpal tunnel syndrome surgery, in work-related cases, it can reasonably be inferred that such surgery, in fact, places the median nerve and other carpal tunnel contents in a position more vulnerable to the forces causing the malady in the first place, yet without the buffering protection of the intact flexor-retinaculum.

Although a number of palliative measures have been advanced as alternatives to surgical intervention, these measures provide very limited, if any, therapeutic benefits. Palliative therapies include for example, volar, i.e., palmar or anterior, splinting, short-arm and transversing the wrist joint; elevation of the wrist; administration of non-steroidal anti-inflammatory drugs, e.g., aspirin, indomethacin and ibuprofen and their progeny; diuretic agents which may be prescribed intermittently; and administration of corticosteroid drugs. Any limited benefits that palliative therapies can provide are provided only very early on in the course of carpal tunnel syndrome or where carpal tunnel syndrome is present in its mildest form. Thus, the effectiveness of palliative therapy is at best, inconsistent, transient or equivocal, and at worst, may be harmful to the patient.

Corticosteroid administration is perhaps the most interventional and controversial among the various palliative measures traditionally employed in the treatment of carpal tunnel syndrome. Towards this end, investigators and clinicians have administered corticosteroid agents both systemically, by mouth or parenterally, and locally, by injection. Regardless of the route or cite of steroid administration employed in the therapeutic endeavor, authoritative texts which speak to this matter have generally been uniformly unenthusiastic in describing the efficacy of corticosteroid drugs in the management of carpal tunnel syndrome.

Since the time corticosteroid injection therapy was first employed in the management of carpal tunnel syndrome over three decades ago, virtually the identical methodology and location of that technique has been repeatedly adopted, without any material change or refinement. Technically, the traditional injection technique as recorded in the medical literature is neither a site specific injection nor a treatment of carpal tunnel syndrome, but merely a local injection at the wrist utilized as a palliative measure in the presence of median nerve entrapment. As shown in photographs and drawings contained within reported medical literature, the traditional mode of injection deposits medication approximate to the median nerve at a point near, at, or beyond the entrapped nerve's exit from the distal canal.

Review of the particular corticosteroid agents and their dosages employed in traditional corticosteroid injections for carpal tunnel syndrome reveals that these drugs are generally short-acting, often of only mild-to-moderate potency, or are administered in inadequate doses. Significantly however is that the direction of conventional injections is the same as the direction of the flow of the blood and synovial fluid. This not only carries the instillant away from the carpal tunnel, but also, since it is proximate to a rich vascular arcade, this type of injection hastens its removal from the site of its local injection into the systemic circulation. This, in no small way, contributes to the transient nature of whatever benefits might be conferred.

Finally, traditional corticosteroid injections are performed only by a limited number of medical specialists, most of whom are the same physicians who perform the carpal tunnel release surgery. A number of potential complications of corticosteroid injection have been advanced; the most serious of which are impalement of the median nerve and chemical neuritis.

It can be seen from the foregoing that it is desirable to have nonoperative techniques and instrumentalities for the treatment of carpal tunnel syndrome which are substantially more effective to those methods of treatment currently used.

It is an object of the present invention to provide techniques and devices for the treatment of carpal tunnel syndrome which are viable alternatives to surgical treatment methods and eliminate the risk and complications associated with carpal tunnel syndrome surgery, in appropriate patients (which includes the majority).

It is also an object of the present invention to provide patients with greater accessibility to effective therapy for the treatment of carpal tunnel syndrome.

Yet another object of the present invention is to provide a method of treatment for carpal tunnel syndrome which significantly reduces the cost of healthcare associated with its treatment.

Still another object of the present invention is to provide a treatment method for carpal tunnel syndrome which eliminates the peri-operative patient pain, inconvenience, and prolonged recuperation associated with traditional treatment methods.

Another object of the present invention is to provide a treatment modality which is effective in cases considered to be prognostically poor for or which have failed surgery.

Yet another object of the present invention is to provide an effective non-surgical treatment method for carpal tunnel syndrome which may be performed by a variety of medical specialists.

These and other objects of the present invention are fulfilled by the novel technique and instrumentality set forth herein.

BRIEF SUMMARY OF THE INVENTION

The novel technique employed in the instant invention entails the use of an apparatus specifically designed to permit delivery of a sustained release, depot form of a corticosteroid agent at an adequate therapeutic dosage, directly into the center of the carpal tunnel. The corticosteroid is delivered by a needle installation directly into the anatomic center of the carpal tunnel in order to produce the desired pharmacological effects associated with the use of corticosteroids. These pharmacological effects include both the early anti-inflammatory effects caused by corticosteroid agents, as well as delayed benefits derived from inhibition of scar formation and fibrinogenesis which are seen as latter positive pharmacotherapeutic manifestations with sustained corticosteroid activity after injection of one of the newer synthetic, long-acting agents. The apparatus for the novel technique herein makes treatment of carpal tunnel syndrome a procedure that can be performed by virtually by any physician. In addition, among the other advantages, the novel technique entails injection at and into a site which is not in proximity to the median nerve itself thereby removing the risk of impalement and chemical neuritis.

BRIEF DESCRIPTION OF THE DRAWINGS

FIG. 5 is a top plan view of the wrist bracket and central needle guide portion of the apparatus shown in FIG. 1.

DETAILED DESCRIPTION OF THE INVENTION

Figure 1:
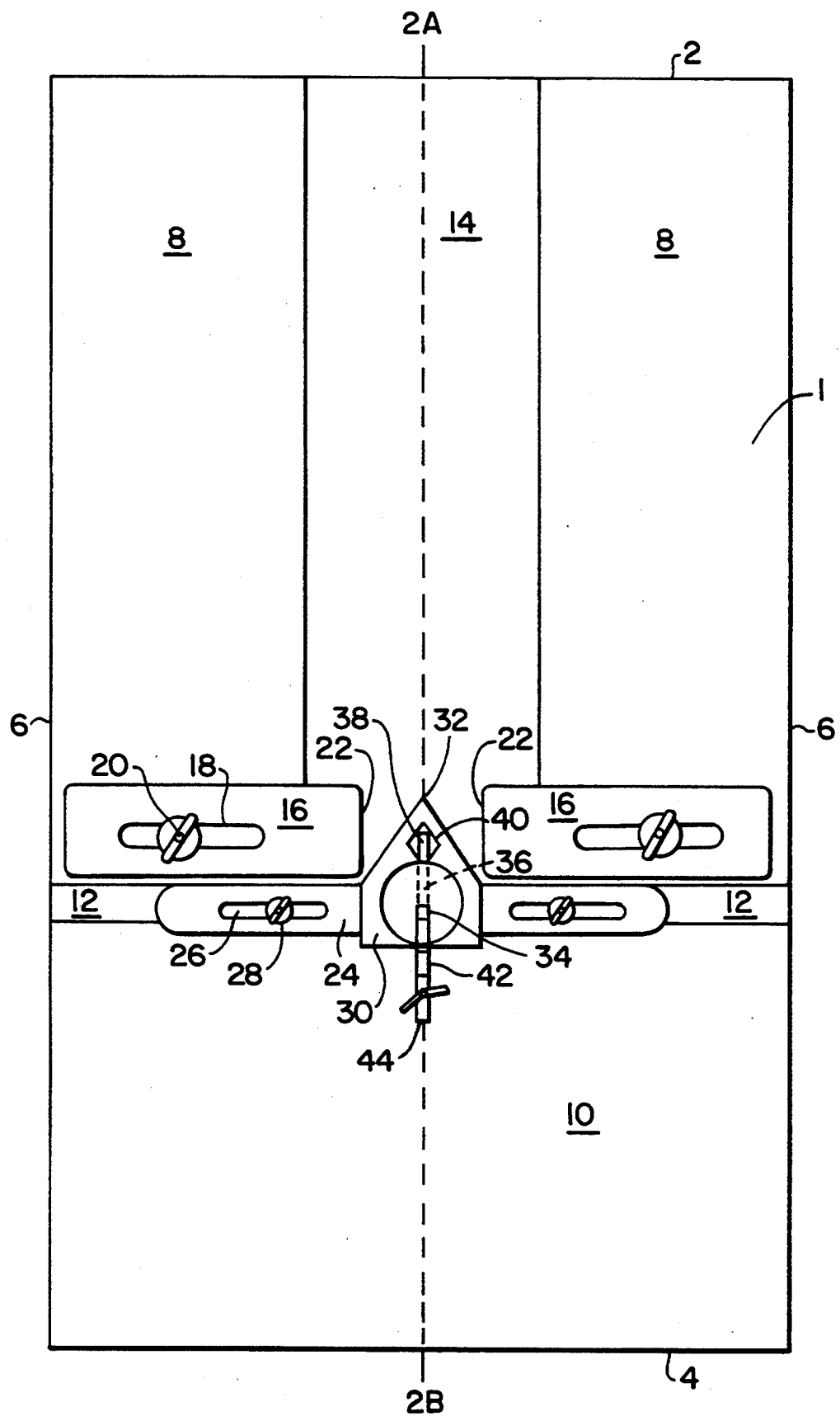
FIG. 1 is a top plan view of an embodiment of the armboard of the instant invention.

In FIG. 1, there is shown one embodiment of the limb-restraint, injection support armboard 1, of the present invention. As depicted in the embodiment shown, armboard 1 is a generally flat, rectangular shape having a proximal end 2, a distal end 4, two side ends 6, an upper planar surface 8, and a lower planar surface 10, separated by wrist flexion curb 12. Upper planar surface 8 and lower planar surface 10 include an arm support member 14, which is preferably a depression or channel, and which may be more preferably, a generally "u-shaped" channel. Arm support member 14 may also be preferably located generally centrally within the body of the armboard. Arm support member 14 is formed so as to receive and generally support the human forearm on upper planar surface 8, and to receive and generally support the hand on lower planar surface 10, of the armboard.

Situated at or near flexion curb 12, preferably on upper planar surface 8 are a pair of adjustable side brackets 16, each having side bracket adjustment slots 18 and side bracket set screws 20. Side bracket set screws 20 permit side brackets 16 to be mounted on armboard 1 and facilitate the adjustment and securing of a human forearm, preferably anchoring the forearm and wrist within arm support member 14, at or near the ulnar and radial styloid processes. In the embodiment depicted, side bracket set screws are wing-nuts; however, other similar mated-thread assemblies and other alternative mounting and securing means may be used including, for example, compression fittings, sliding fasteners, or ratcheted post and guides.

Preferably, side brackets 16 are located directly opposite each other and are moveable in an inward-outward direction relative to each other, as well as in planar arcuate directions. Side brackets 16 include forearm positioning surfaces 22, which may be contoured, cushioned or otherwise molded to firmly secure a forearm in place with minimum discomfort to the patient. In other, alternate embodiments of the armboard of the present invention, one of the side brackets may be fixed in-place with the other being adjustable in the manner described above, so as to allow adjustment of the forearm to occur at one side of the forearm with the opposite side bracket being essentially stationary. In other embodiments of the armboard of the instant invention, alternative securing means for securing the forearm and wrist may be used, including, for example, clamps or straps which may include hook and pile, velcro-type fasteners.

When in use, a patient's forearm and hand is placed in the armboard, palmar side-up and is positioned in arm support member 14 so that the wrist will lie approximately at or near wrist flexion curb 12. Wrist flexion curb 12 facilitates proper flexion of a patient's wrist to generally expose and provide access to the carpal tunnel. Proper placement will put the patient's hand in a range of approximately 10 to 30 degrees of dorsi-flexion, with the preferred degree of dorsi-flexion of approximately 20 degrees. Wrist flexion curb 12 may be incorporated in the armboard as a slope or ramp with the appropriate angular orientation or it may be an angular 90 degree drop-off or ledge of not more than roughly 3 inches between the upper and lower planar surfaces. Wrist placement may also be further facilitated by the use of positioning blocks, wedges or other shapes including those dictated by patient comfort considerations, which may be placed under the hand and/or forearm.

Positioned at or near flexion curb 12 and preferably above the plane of side brackets 16, is wrist bracket 24. Wrist bracket 24 includes a pair of wrist bracket adjustment slots 26, and may also include central needle guide 30 which may be mounted directly to armboard 1, via wrist bracket adjustment screws 28. In alternate preferred embodiments, wrist bracket 24 may be offset and mounted above side brackets via side bracket adjustment screws 28. In other alternative embodiments, wrist bracket 24 may have only a single adjustment slot for mounting and adjustment. In these embodiments, the wrist bracket remains essentially adjustable in the manner described above. Still, in other alternative embodiments, needle guide 30 may be mounted onto the armboard, separately and apart from wrist bracket 24.

Located generally centrally within wrist bracket 24 is needle guide 30. Guide 30 includes at its proximal side edge centering pointer 32, needle entrance 34, needle channel 36 (shown in outline detail) and needle exit 38. Needle channel 36 lies between needle entrance 34 and needle exit 38. Centering pointer 32 also includes viewing aperture 40 for viewing needle insertion between the two central tendons of a patient's forearm. In one preferred embodiment of the present invention, viewing aperture 40 is simply a opening or void in the centering pointer. In other preferred embodiments, viewing aperture 40 may include a magnifying lens and/or lighting means to facilitate viewing of a needle injection site prior to the needle's insertion into a patient's forearm. Needle entrance 34 is preferably constructed so as to permit insertion there through a flexible sterile needle and through which a drug delivery canula, also preferably flexible, may be passed into the needle interior and ultimately to the carpal tunnel. Upon insertion of the flexible sterile needle into the needle entrance, through the channel and out of the needle exit, a medication delivery tube will typically be inserted therein with the needle being then withdrawn from the injection site. A preferred medication dosage formula may then be infused directly into the injection site. In one preferred embodiment, needle entrance 34 may also include at the end opposite the needle channel, needle hub 42 and syringe adapter 44. Needle hub 42 facilitates attachment of syringe adapter 44 to a cannula or conduit which may be used to infuse an injection site. Syringe adapter 44 is a multi-way valve, such as a three-way stopcock valve, which permits infusion of medication from syringes 46 and 48. In other preferred embodiments, a single needle and syringe may be used to deliver medication to the carpal tunnel.

Armboard 1, and its major component structural parts are preferably made of rigid or semi-rigid materials from which the apparatus made be easily and economically fabricated. Suitable materials for the construction of the apparatus or its component parts include, for example, nylon, ABS, or other light-weight durable plastics or may be made of metal, including aluminum, stainless steel or other materials, including reinforced fiberglass, ceramic composites, or combinations of these materials which are capable of withstanding both repeated use and sterilization processes whether by heat or chemicals. Moreover, the various component parts, such as side brackets, forearm positioning surfaces, wrist brackets and needle guides may also be made in different sizes to accommodate the forearm sizes of a variety of patients, for example, as between younger and older patients or between male and female patients.

Finally, in other preferred embodiments of the armboard of the instant invention, the forearm bearing surface of armboard 1 may be constructed so to form a pair of opposed inclines or ramps, with the wrist flexion curb forming the apex of the two inclines. The incline forming the upper planar surface will support the forearm proper and the incline forming the lower planar surface will support the hand. In these embodiments, the wrist will be placed at the wrist flexion curb with the forearm and hand resting on the arm support member in the manner described above.

Figure 2:
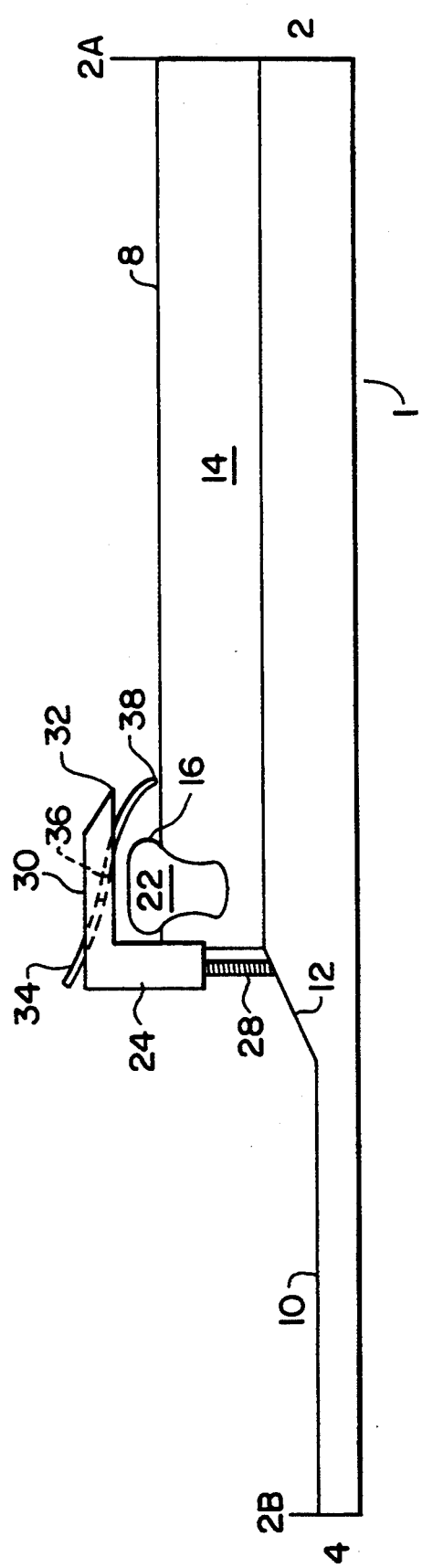
FIG. 2 is a side cross-sectional view of the apparatus of FIG. 1 at line 2a–2b.

In FIG. 2 is shown a side cross-sectional view of the armboard of FIG. 1 at line 2a–2b. The portion of armboard 1 including proximal end 2, generally carries upper planar surface 8, whereas the portion designated distal end 4, includes lower planar surface 10. Shown in partial outline is arm support member 14, depicted as a generally "u-shaped" channel defined at its upper surface edge by upper planar surface 8. Arm support member 14 is preferably of sufficient depth to permit a patient's forearm to rest securely therein. Separating upper and lower planar surfaces is wrist flexion curb 12, generally shown as a slope having an angle of between 10 to 30 degrees, and preferably, having a slope of approximately 20 degrees.

Positioned at or near flexion curb 12, is adjustable side bracket 16. In the embodiment shown in FIG. 2, side bracket 16 is moveable in an inward-outward direction relative to the plane of the drawing, as well as being moveable in an arcuate direction across the drawing plane. Side bracket 16 includes forearm positioning surface 22, which may be contoured, cushioned or otherwise adapted to firmly secure a forearm in place, preferably anchoring the forearm at the ulnar and radial styloid portions. Side bracket 16 is adjustable via bracket adjustment slots 18 (not shown) and side bracket set screws 20 (shown in phantom detail). In alternate embodiments, one side bracket may be non-moveable, so as to allow securing and adjustment of the forearm to occur only on one side of the forearm with the member of the opposite side bracket pair being adjustable.

Positioned at or near flexion curb 12 and at the terminus of arm support member 14 is wrist bracket 24. Wrist bracket 24 includes central needle guide 30. In the embodiment shown, wrist bracket 24 is mounted to armboard 1, via a pair of wrist bracket adjustment screws 28. In alternate embodiments, wrist bracket 24 may have only a single adjustment slot and screw for mounting and adjustment. Guide 30 includes at its proximal side edge centering pointer 32, needle entrance 34, needle channel 36 (shown in phantom detail) and needle exit 38. Needle channel 36 lies between needle entrance 34 and needle exit 38.

Figure 3:
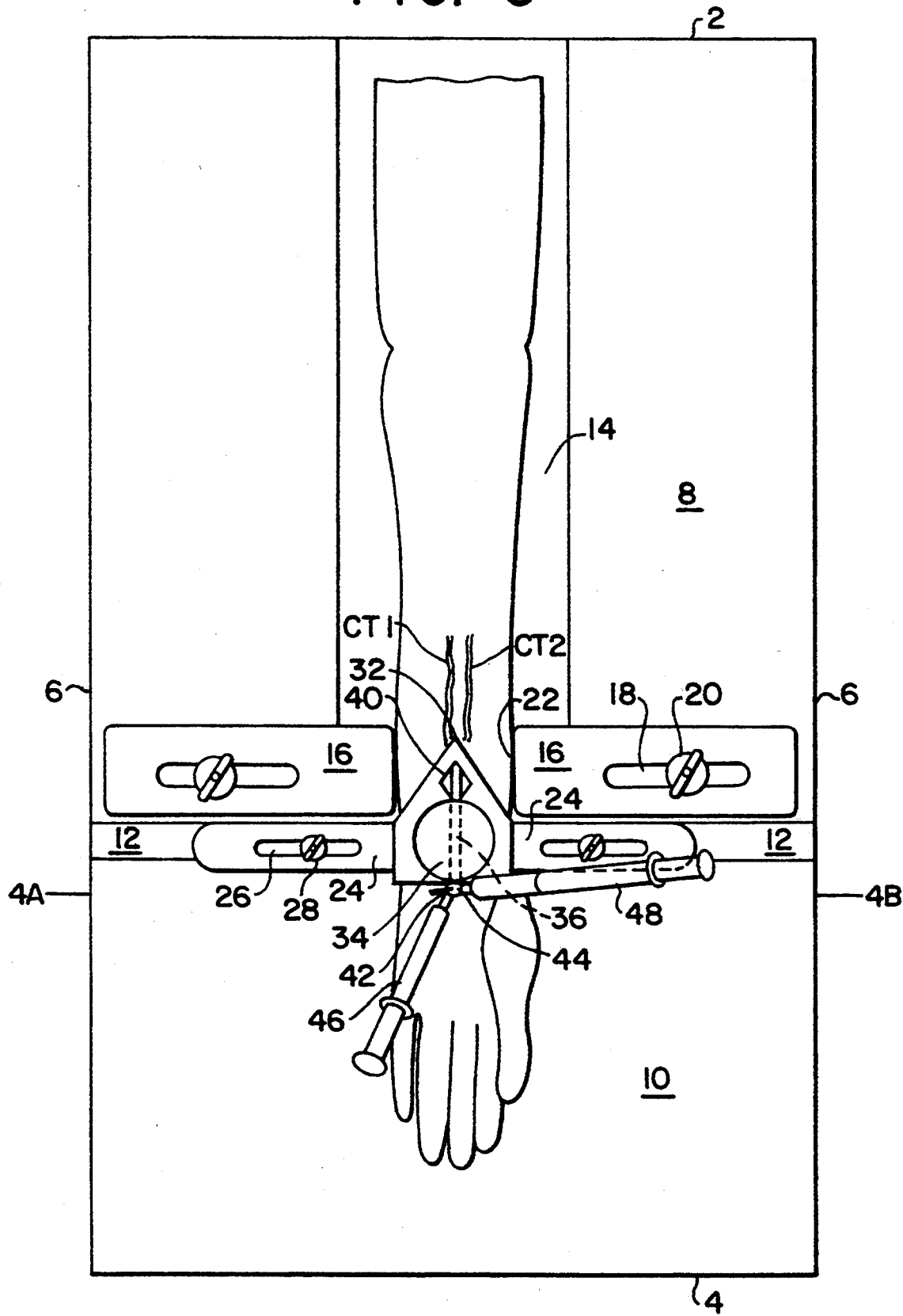
FIG. 3 is a top plan view of the apparatus of FIG. 1, shown with a representation of a human forearm and hand.

FIG. 3 shows a top plan view of the apparatus of FIG. 1, shown with a representation of a human forearm and hand. When the armboard is in use, the forearm and hand may be placed in the centrally located arm support member 14, with the elbow portion of the forearm situated at or near proximal end 2. The forearm and hand are positioned palmar side-up and are advanced towards distal end 4 of armboard 1, until the point of transition occurring at wrist flexion curb 12. By placing the flexor-palmar crease of the wrist portion of the forearm at wrist flexion curb 12, the wrist will be in approximately 20 degrees of dorsi-flexion, thereby providing access to the carpal tunnel from between the two central tendons, designated CT-1 and CT-2. After the wrist is in proper placement at wrist flexion curb 12, side brackets 16 are moved inwardly to bring forearm positioning surfaces 22 in contact with the lateral surfaces of the forearm, preferably at the ulnar and radial styloids. The forearm is then secured in place by side brackets 16 via side bracket adjustment screws 18.

After securing the forearm in place, wrist bracket 24, carrying central needle guide 30 is brought into position over the forearm. Typically the patient's forearm may then be prepared for sterile technique as is well-known in the art. Wrist bracket 24 further secures the forearm at the palmar surface of the wrist by providing downward force on that surface which may be adjusted by wrist adjustment screws 28. As part of securement of the wrist, centering pointer 32 is brought into position between the two central tendons of the forearm. Centering pointer 32 includes viewing window 40 for visual inspection of the injection site on the forearm above the carpal tunnel. After proper placement of centering pointer 32 and after wrist bracket 24 is secured in place, a flexible needle is advanced into needle entrance 34, through needle channel 36 and out of needle exit 38. Preferably, the flexible needle used will be of sufficient length to traverse the entire length of the needle guide without requiring excessive compression of the forearm by wrist bracket 24 in order to reach the carpal tunnel. Typically, the needle used will be from 20 to 26 gauge and will be from 1 to 3 inches in length, preferably 1.5 to 2 inches, depending on the size of the patient's forearm, the configuration of the wrist bracket assembly and the placement of the forearm within the forearm channel. It is important however, to bear in mind that the needle need only be of sufficient length to permit the needle tip to enter into the midpoint of the carpal tunnel without proceeding at all into the median nerve. After the injection site is identified, the site may be prepared with a topical anesthetic spray or subcutaneous injection of a small dose of local anesthetic, prior to infusion of other medications.

In one preferred embodiment of the method of use of the instant invention, after the needle is properly placed into the carpal tunnel of the afflicted extremity, a sterile, flexible plastic conduit or cannula 50 (not shown) may be introduced into the interior of the flexible needle and then passed through to the terminus of the injection site. The needle tip may then be withdrawn while leaving the flexible cannula 50 in place in the carpal tunnel. The cannula end opposite the injection site end may then be fitted with a needle-hub and connected to a syringe or other delivery means for providing appropriate medication directly to the carpal tunnel.

In a preferred embodiment of the method herein, syringe adapter 44 may be connected to the conduit end opposite the injection site end of flexible cannula 50. Preferably this will be a multi-way valve, and more preferably, a three-way valve connected at one port to cannula 50 and at each of the remaining two ports to syringes 46 and 48, one of which contains a local, moderate to long duration injectable anesthetic and the other of which contains a corticosteriodal preparation, respectively.

In this preferred embodiment, syringe 46 is a 5 cc. syringe containing roughly 3 to 5 cc. of a long-acting, local anesthetic agent. Suitable anesthetic agents include those which are non-irritating to the tissue to which they are applied and which do not cause any permanent damage to the nerve structures, such as for example, Lidocaine, mepivacaine or bupivacaine. One preferred agent is a long duration Mepivacaine 5% solution. Syringe 48 is also a 5 cc. syringe containing a long-acting depot form of a synthetic corticosteroid ester. Suitable corticosteroids are those which possess high anti-inflammatory relative potencies such as, for example, prednisolone, methyl-prednisolone, triamcinolone and dexamethasone, marketed under the trade names Hydeltrasol, Hydelta-T.B.A., Depo-Medrol, Medrol Acetate, Aristocort Diacetate and Decadron L.A. One preferred corticosteroid is methyl-prednisolone administered at a dosage range of approximately 1 to 2 milligrams per kilogram of body weight of the patient, preferably at 1.4 to 1.6 milligrams per kilogram per injection.

Following insertion of the cannula and attachment of multi-way valve syringe adapter 44 and syringes 46 and 48, the lever on the valve is set to permit introduction of the long-acting anesthetic from syringe 46 into the injection site. After supplying sufficient local anesthetic into the carpal tunnel, the lever is then moved to permit introduction of the corticosteroid dosage from syringe 48 into the carpal tunnel. After supplying the corticosteroid, the cannula is withdrawn, the needle guide is removed and the forearm is removed from the armboard. In conformity with sterile technique, it is also desirable to apply a topical antibiotic and bandage to the injection site. In some instances, it may also be desirable to apply a volar splint to immobilize the hand and forearm for an eight to twelve hour period before resuming normal activities with the afflicted extremity. The procedure may also be repeated on the opposite extremity where bi-lateral symptomatology is present.

Figure 4:
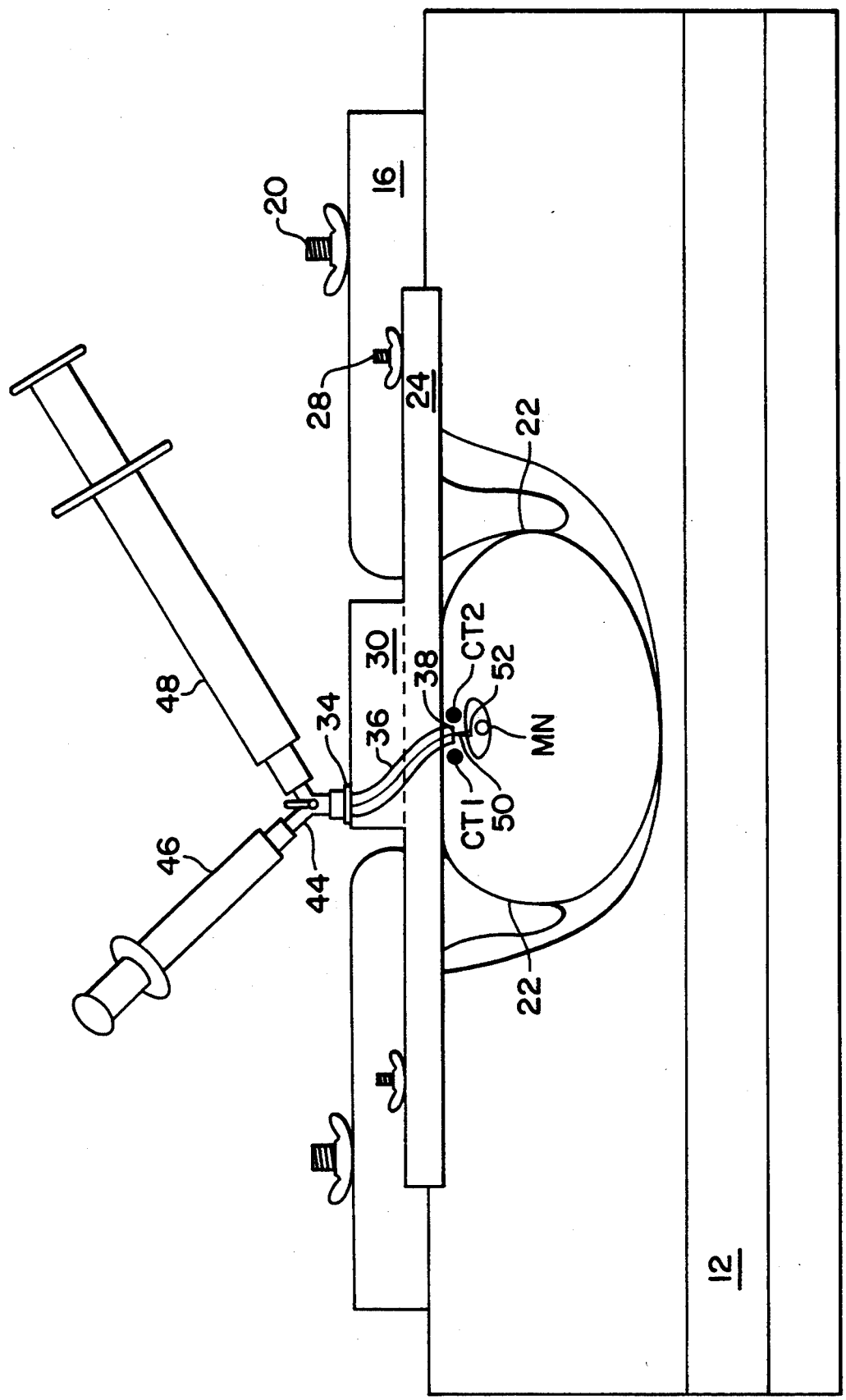
FIG. 4 is a cross-sectional schematic view of the apparatus shown in FIG. 3, taken along the lines 4a–4b.

FIG. 4 shows a cross-sectional schematic view of the apparatus shown in FIG. 3, taken along the lines 4a–4b. By placing the flexor-palmar crease of the wrist portion of the forearm at wrist flexion curb 12, the wrist is in approximately 20 degrees of dorsi-flexion. Side brackets 16 have been moved inwardly to bring forearm positioning surfaces 22 in contact with the lateral surfaces of the forearm, preferably at the ulnar and radial styloids. Wrist bracket 24, carrying central needle guide 30 is positioned over the forearm, thereby providing a visual cue as to the location of the carpal tunnel from between the two central tendons, indicated by the designations CT-1 and CT-2. Wrist bracket 24 rests on the forearm on the palmar surface of the wrist and provides downward force on that surface to partially immobilize the wrist. After proper placement of centering pointer of wrist bracket 24, a flexible needle is advanced into needle entrance 34, through needle channel 36 (shown in phantom detail) and out of needle exit 38. A flexible needle of sufficient length to traverse the entire length of the needle guide and permit the needle tip to enter into the carpal tunnel without proceeding into the median nerve is used in needle guide 30. Syringe adapter 44 and syringes 46 and 48 are shown at needle entrance 34. Cannula 50 having cannula terminus end 52 is shown located in the carpal tunnel at a point cephalad to the median nerve (MN).

In FIG. 5 there is shown a top plan view of the wrist bracket and needle guide portion of the apparatus of FIG. 1. Wrist bracket 24, includes central needle guide 30 and a pair of wrist bracket adjustment slots 26 for mounting the bracket to armboard 1 and for lateral adjustment of the needle guide. Central needle guide 30 includes centering pointer 32, needle entrance 34, needle channel 36 (shown in phantom detail) and needle exit 38. Centering pointer 32 includes viewing aperture 40 for visual inspection of the injection site on the forearm anterior to the carpal tunnel. As can be seen, needle exit 38 is located at or within viewing aperture 40 and is situated at or near the proximal side end of wrist bracket 24. Needle channel 36 is of sufficient length to allow an associated flexible needle to traverse the entire length of the needle guide, exiting at needle exit 38, and to permit the needle tip to reach the midpoint of the carpal tunnel. Channel needle 36 is also of sufficient bore to accommodate from 20 to 26 gauge needles and is preferably from 0.75 to 2.5 inches in length, from its starting point at needle entrance 34 to needle exit 38. In one preferred embodiment, needle channel 36 is also curved downwardly, so that needle exit 38 is generally perpendicular to a proposed injection site. In other preferred embodiments, needle exit 38 may also be from approximately 20 to 80 degrees off perpendicular, depending on, for example, the configuration of the wrist bracket itself, the angle of the slope or ledge of the wrist flexion curb and the location of the forearm and hand within the armboard. In other preferred embodiments, the needle guide 30 may be made removable from wrist bracket 24. After the forearm and wrist are properly positioned by the wrist bracket, the needle guide may be placed in an opening adapted to receive the needle guide, within the wrist bracket.

The foregoing descriptions are illustrative of the preferred embodiments shown. The descriptions are not intended to limit the present invention to the specific apparatuses and techniques shown and described, but instead it will be appreciated that adaptations and modifications will become apparent from the present disclosure which are intended to be within the scope of the claims as set forth below.

What I claim is:

1. A method of treating carpal tunnel syndrome in humans comprising:
    (a) employing an instrument having:
        (i) a base for supporting a human arm consisting of a forearm, wrist and hand, said base having top surface and a bottom surface, said top surface having an arm support member, an upper planar surface and a lower planar surface, said upper and lower planar surfaces being separated by a wrist flexion curb, said base forming an armboard;
        (ii) first means affixed to the base for securing the forearm portion of said arm to said armboard;

(iii) second means affixed to the base for securing the wrist portion of said arm to said armboard; and
(iv) a needle guide;
(b) positioning a human arm, palmar side-up within said arm support member so that said wrist portion is approximately at 20 degrees of dorsi-flexion;
(c) securing said arm to said board with said first means;
(d) securing said wrist to said board with said second means;
(e) positioning said needle guide above an injection site on the palmar surface of said forearm, said site corresponding to the location of the carpal tunnel within said forearm;
(f) inserting a needle into said needle guide and into said forearm at said injection site, so that said needle tip does not extend beyond the anatomical center of said carpal tunnel;
(g) injecting a liquid containing a corticosteroid into said injection site;
(h) removing said needle from said injection site and needle guide; and
(i) releasing said arm from said armboard.

2. The method of claim 1 wherein said first means comprises at least one forearm bracket which is moveable inwardly towards a styloid portion of the wrist of said arm.

3. The method of claim 1 wherein said second means comprises a wrist bracket.

4. The method of claim 3 wherein said wrist bracket includes said needle guide, said guide including a centering pointer, a viewing aperture, a needle entrance, a needle channel and a needle exit.

5. The method of claim 4 wherein the step of positioning the needle guide further comprises the step of locating said injection site with reference to an anatomical landmark corresponding to the area between central tendons located within said forearm by viewing said site through said viewing aperture.

6. The method of claim 1 wherein the step of injecting further comprises the step of injecting a local anesthetic at said injection site prior to injecting said corticosteroid.

7. The method of claim 6 wherein said anesthetic is selected from the group consisting of Lidocaine, Mepivacaine and Bupivacaine and said corticosteroid is methyl-prednisone.

8. A method of treating carpal tunnel syndrome in humans comprising:
(a) placing a human arm consisting of a forearm, wrist and hand on an armboard;
(b) positioning said human arm, palmar side-up on said armboard such that the wrist is approximately 20 degrees of dorsiflexion to provide access to the carpal tunnel within said arm;
(c) securing said arm to said arm board;
(d) locating the carpal tunnel on the palmar surface of said arm;
(e) positioning a needle above an injection site on said arm, said site corresponding to the location of the carpal tunnel within said arm;
(f) inserting a needle into said arm at said injection site, so that said needle tip does not extend beyond the anatomical center of said carpal tunnel;
(g) injecting a liquid containing a corticosteroid into said injection site;
(h) removing said needle from said injection site; and
(i) releasing said arm from said armboard.

* * * * *